(12) United States Patent
Jiang

(10) Patent No.: US 8,648,187 B2
(45) Date of Patent: Feb. 11, 2014

(54) METHOD FOR SEPARATION OF DOUBLE-STRANDED AND SINGLE-STRANDED NUCLEIC ACIDS FROM THE SAME SAMPLE

(75) Inventor: Miao Jiang, Cedar Knolls, NJ (US)

(73) Assignee: GE Healthcare Bio-Sciences Corp., Piscataway, NJ (US)

(*) Notice: Subject to any disclaimer, the term of this patent is extended or adjusted under 35 U.S.C. 154(b) by 315 days.

(21) Appl. No.: 12/999,325

(22) PCT Filed: Jun. 2, 2009

(86) PCT No.: PCT/US2009/045934
§ 371 (c)(1),
(2), (4) Date: Dec. 16, 2010

(87) PCT Pub. No.: WO2009/155128
PCT Pub. Date: Dec. 23, 2009

(65) Prior Publication Data
US 2011/0092692 A1    Apr. 21, 2011

Related U.S. Application Data

(60) Provisional application No. 61/073,379, filed on Jun. 18, 2008.

(51) Int. Cl.
*C07H 21/02* (2006.01)
*C07H 21/04* (2006.01)

(52) U.S. Cl.
CPC ............... *C07H 21/02* (2013.01); *C07H 21/04* (2013.01)
USPC ..................................... 536/25.4; 536/25.42

(58) Field of Classification Search
None
See application file for complete search history.

(56) References Cited

U.S. PATENT DOCUMENTS

| 6,180,778 B1 * | 1/2001 | Bastian et al. ............... 536/25.4 |
| 7,888,006 B2 * | 2/2011 | Lenz ............................ 435/6.16 |
| 2008/0026451 A1 | 1/2008 | Braman et al. | |

OTHER PUBLICATIONS

Qiagen: "AllPrep DNA/RNA/Protein Mini Handbook, AllPrep DNA/RNA/Protein Procedure", Internet Citation, Dec. 2007, pp. 1-60, URL: http://www.qiagen.com [retrieved on Feb. 23, 2009].
Extended EP Search Report Issued on Corresponding Application No. 09767439.4 Dated Oct. 27, 2011.

* cited by examiner

*Primary Examiner* — Eric S Olson

(57) ABSTRACT

The invention provides systems, methods and kits for the separation and/or purification of double-stranded and single-stranded nucleic acids from the same sample. The method includes first mixing a sample containing both double-stranded nucleic acid and single-stranded nucleic acid with a solution including a chaotropic salt and a non-ionic detergent to generate a mixture; then applying the mixture to a first mineral support for double-stranded nucleic acid to bind; and collecting the flow-through which contains unbound single-stranded nucleic acid. The method further includes diluting the non-ionic detergent of the flow-through, and applying the diluted flow-through to a second mineral support for the single-stranded nucleic acid to bind. Alternatively the flow-through can be mixed with a lower aliphatic alcohol prior to loading of the second column. The double-stranded and the single-stranded nucleic acids can be eluted from the mineral supports respectively.

17 Claims, 2 Drawing Sheets

METHOD FOR SEPARATION OF DOUBLE-STRANDED AND SINGLE-STRANDED NUCLEIC ACIDS FROM THE SAME SAMPLE

CROSS-REFERENCE TO RELATED APPLICATIONS

This application is a filing under 35 U.S.C. §371 and claims priority to international patent application number PCT/US2009/045934 filed Jun. 2, 2009, published on Dec. 23, 2009 as WO 2009/155128, which claims priority to U.S. provisional patent application No. 61/073,379 filed Jun. 18, 2008; the disclosure of which is incorporated herein by reference in its entirety.

FIELD OF THE INVENTION

This invention relates to methods for the separation of double-stranded and single-stranded nucleic acids. More specifically, it relates to a simple and rapid system and method for the separation and purification of double-stranded nucleic acid such as DNA from single-stranded nucleic acid such as RNA.

BACKGROUND OF THE INVENTION

The last three decades has seen considerable effort in the development of improved methods for the isolation and purification of nucleic acids. This has been due mainly to the increasing applications of nucleic acids in the medical and biological sciences. Genomic DNA isolated from blood, tissue or cultured cells has several applications, which include PCR, sequencing, genotyping, hybridization and southern blotting. Plasmid DNA has been utilized in sequencing, PCR, in the development of vaccines and in gene therapy. Isolated RNA has a variety of downstream applications, including in vitro translation, cDNA synthesis, RT-PCR and for microarray gene expression analysis.

The analysis and in vitro manipulation of nucleic acids is typically preceded by an isolation step in order to free the samples from unwanted contaminants which may interfere with subsequent processing procedures. For the vast majority of procedures in both research and diagnostic molecular biology, extracted nucleic acids are required as the first step.

The increased use of DNA and RNA has created a need for fast, simple and reliable methods and reagents for isolating DNA and RNA. In many applications, collecting the biological material sample and subsequent analysis thereof would be substantially simplified if DNA and RNA could be simultaneously isolated from a single sample. The simultaneous isolation is especially important when the sample size is so small, such as in biopsy, that it precludes its separation into smaller samples to perform separate isolation protocols for DNA and RNA.

Also needed is an improved process for separating double-stranded from single-stranded nucleic acids in general. Many nucleic acid molecular biology experiments start from purified nucleic acids and produce a mixture containing both. A separation step is required at the end of many of these experiments and sometimes both the single-stranded and the double-stranded nucleic acids need to be recovered for further analysis.

Currently, the silica membrane column format is widely used for separating and isolating double-stranded and single-stranded nucleic acids. However alcohol is required as a binding reagent, which posts a safety concern as it is flammable.

A novel and advantageous method for carrying out separation and isolation of double-stranded and single-stranded nucleic acids from the same sample is presented herein.

SUMMARY OF THE INVENTION

In general, the instant invention provides improved methods, systems and kits for rapid separation and isolation of double-stranded and single-stranded nucleic acids from the same sample. The double-stranded nucleic acid is selectively adsorbed to a mineral support in the presence of high concentration of chaotropic salt and non-ionic detergent. The flow-through containing single-stranded nucleic acid is adjusted so that single-stranded nucleic acid is adsorbed to a second mineral support. The nucleic acids are then optionally eluted from each of the mineral supports respectively.

Thus, one aspect of the invention provides a method for the separation and/or purification of double-stranded nucleic acid and single-stranded nucleic acid from a sample. The method includes first mixing a sample containing both the double-stranded nucleic acid and the single-stranded nucleic acid with a solution containing a chaotropic salt and one or more non-ionic detergent to generate a mixture; then applying the mixture to a first mineral support for double-stranded nucleic acid to bind; and collecting the flow-through which contains unbound single-stranded nucleic acid. The method further includes diluting the concentration of the non-ionic detergent of the flow-through; then loading the adjusted flow-through to a second mineral support for the single-stranded nucleic acid to bind. Alternatively the flow-through can be mixed with a lower aliphatic alcohol followed by loading to and purification from a second column.

In certain embodiments, the method further comprises eluting the double-stranded nucleic acid from the first mineral support after a wash step. In other embodiments, the method also includes eluting the single-stranded nucleic acid from the second mineral support after a wash step In another aspect, the invention provides a kit for separating and isolating double-stranded nucleic acid and single-stranded nucleic acid. The kit includes a solution containing a chaotropic salt and one or more non-ionic detergent for sample processing; a first mineral support for binding the double-stranded nucleic acid; a second mineral support for binding the single-stranded nucleic acid; an optional elution solution for eluting the double-stranded nucleic acid from the first mineral support; and an optional elution solution for eluting single-stranded nucleic acid from the second mineral support. Optionally, the kit also includes wash solutions for washing the respective mineral supports prior to elution.

In a preferred embodiment, the first mineral support and the second mineral support are each silica membranes.

The above and further features and advantages of the instant invention will become clearer from the following detailed description and claims.

DETAILED DESCRIPTION OF THE INVENTION

Figure 1:
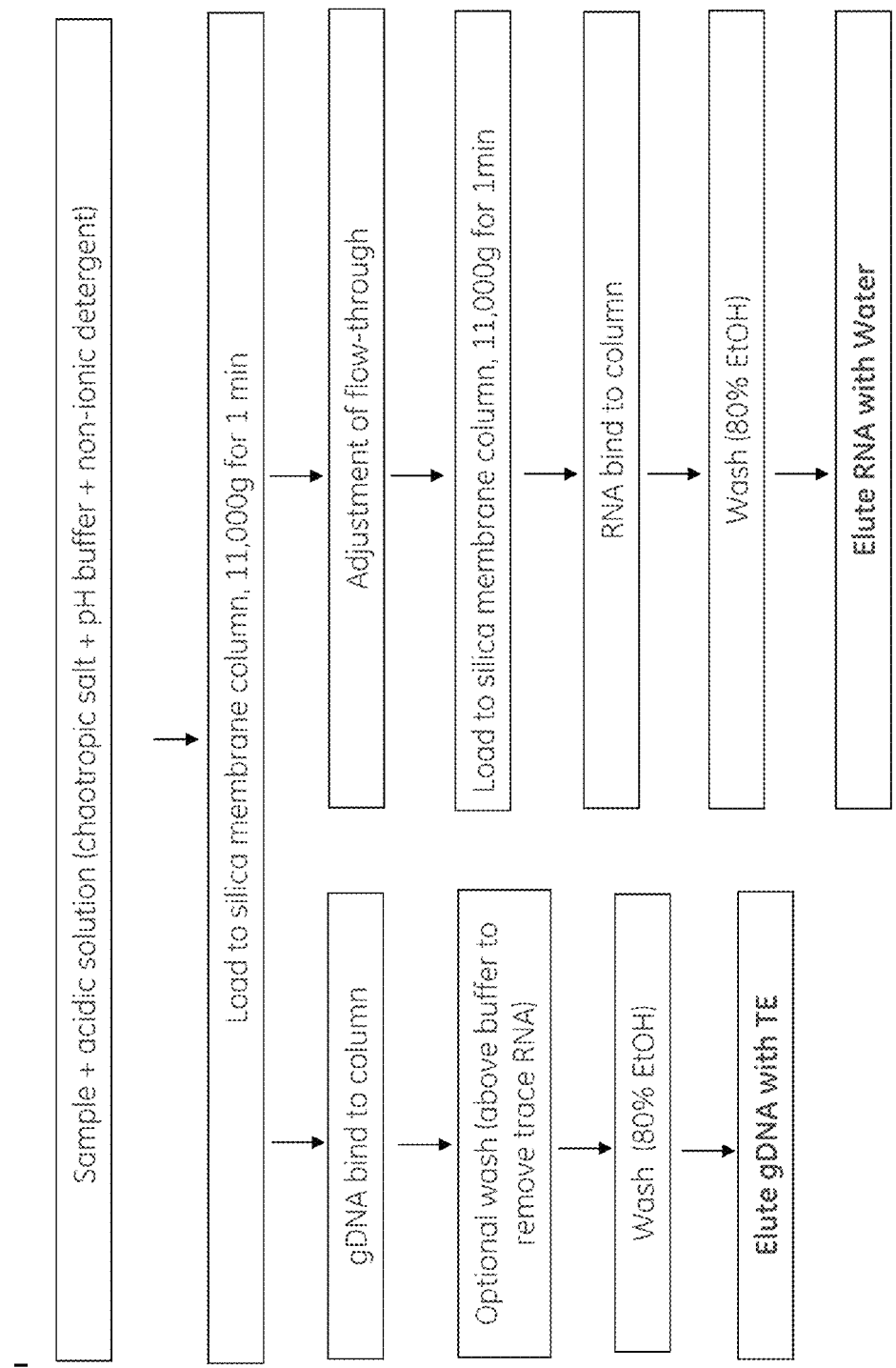
FIG. 1 presents a schematic diagram of the method for the separation and purification of double-stranded and single-stranded nucleic acids from a sample, according to an embodiment of the invention.

The present invention provides compositions, methods, and kits for highly effective, simple separation of double-stranded and single-stranded nucleic acids from the same sample. The nucleic acids can be isolated utilizing the methods of the invention in as little as 10 minutes. The resulting double-stranded and single-stranded nucleic acids are of high quality suitable for use in downstream applications.

The invention is well suited for the separation of double-stranded and single-stranded nucleic acids from a broad range of samples. These include a variety of biological sources such as, without limitation, whole tissues, including biopsy materials and aspirates; in vitro cultured cells, including primary and secondary cells, transformed cell lines, and tissue and blood cells; and body fluids such as urine, sputum, semen, secretions, eye washes and aspirates, lung washes and aspirates. Fungal and plant tissues, such as leaves, roots, stems, and caps, are also within the scope of the present invention. Microorganisms and viruses that may be present on or in a biological sample are within the scope of the invention. Bacterial cells are also within the scope of the invention. Also included are certain molecular biology reaction mixtures that contain both double-stranded and single-stranded nucleic acids.

In its broadest aspects, the invention encompasses methods for separation and purification of double-stranded and single-stranded nucleic acids from the same sample, wherein double-stranded nucleic acid is selectively adsorbed to a mineral support in the presence of high concentration chaotropic salt and non-ionic detergent. This is followed by reducing the concentration of the non-ionic detergent in the flow-through so that single-stranded nucleic acid is adsorbed to a second mineral support. Alternatively the flow-through can be mixed with a lower aliphatic alcohol followed by loading to and purification from a second column. As an example, the double-stranded nucleic acid can be genomic DNA, while the single-stranded nucleic acid can be RNA such as total RNA.

Accordingly, a sample solution containing both the double-stranded and single-stranded nucleic acids is admixed first with a solution containing a suitable chaotropic salt and non-ionic detergent. The mixture is applied to a first mineral support under conditions for the double-stranded nucleic acid (e.g., genomic DNA) to bind; while the flow-through containing unbound single-stranded nucleic acids (e.g., total RNA) is collected. The follow-through is applied to a second mineral support under conditions for single-stranded nucleic acids to bind (e.g., by lowering the concentration of the non-ionic detergent or mixing with a lower aliphatic alcohol). Double-stranded and single-stranded nucleic acids are eluted from the first and second mineral support, respectively. An example workflow according to an embodiment of the invention is presented in FIG. 1.

The term "chaotrope" or "chaotropic salt," as used herein, refers to a substance that causes disorder in a protein or nucleic acid by, for example, but not limited to, altering the secondary, tertiary, or quaternary structure of a protein or a nucleic acid while leaving the primary structure intact. Exemplary chaotropes include, but are not limited to, guanidine hydrochloride, guanidinium thiocyanate, sodium thiocyanate, sodium iodide, sodium perchlorate, potassium iodide and urea. A typical anionic chaotropic series, shown in order of decreasing chaotropic strength, includes: $CCl_3COO^- \rightarrow CNS^- \rightarrow > CF_3COO^- \rightarrow ClO_4^- > I^- \rightarrow CH_3COO^- \rightarrow Br^-$, $Cl^-$, or $CHO_2^-$.

The term "lower aliphatic alcohol" as used herein is intended to refer to $C_1$-$C_3$ alcohols such as methanol, ethanol, n-propanol, or isopropanol. Preferably, the lower aliphatic alcohol is ethanol or an aqueous ethanol mixture.

One of the most important aspects in the purification of RNA is to prevent its degradation during the procedure. Therefore, the current solutions for separating the double-stranded and single-stranded nucleic acids are preferably solutions containing large amounts of chaotropic ions. This solution immediately inactivates virtually all enzymes, preventing the enzymatic degradation of RNA. The solution contains chaotropic substances in concentrations of from 0.1 to 10 M. As said chaotropic substances, there may be used, in particular, salts, such as sodium perchlorate, guanidinium chloride, guanidinium isothiocyanate/guanidinium thiocyanate, sodium iodide, potassium iodide, and/or combinations thereof.

Optionally, the solution also includes a reducing agent which facilitates denaturization of RNase by the chaotropes and aids in the isolation of undegraded RNA. Preferably, the reducing agent is 2-aminoethanethiol, tris-carboxyethylphosphine (TCEP), or beta-mercaptoethanol.

The solution used in the present invention preferably also contains a sufficient amount of buffer to maintain the pH of the solution. The pH should be maintained in the acidic range of about 4-6. The preferred buffers for use in the solution include tris(hydroxymethyl)aminomethane hydrochloride (Tris-HCl), sodium phosphate, sodium acetate, sodium tetraborate-boric acid and glycine-sodium hydroxide.

In a most preferred embodiment, an acidic pH, buffered solution includes 7 M guanidine HCl, 50 mM Tris, at pH 5.

By serendipity we found that single-stranded nucleic acid does not bind to the mineral support in our acidic buffer solution that contains a high concentration of non-ionic detergent, whereas double-stranded nucleic acid does. Therefore, when a sample containing both double-stranded and single-stranded nucleic acid is admixed with such a solution, only the double-stranded nucleic acid (e.g., genomic DNA) binds to a mineral support, while single-stranded nucleic acid (e.g., total RNA) does not bind and is easily separated.

Exemplary non-ionic detergents/surfactants include, but are not limited to, t-octylphenoxy-polyethoxyethanol (TRITON® X-100), (octylphenoxy)polyethoxyethanol (IGEPAL® CA-630/NP-40), triethyleneglycol monolauryl ether (BRIJ® 30), sorbitari monolaurate (SPAN® 20), or the polysorbate family of chemicals. The polysorbate family of chemicals, such as TWEEN® 20, is a preferred group of non-ionic detergents. Other commercially available polysorbates include TWEEN® 40, TWEEN® 60 and TWEEN® 80 (Sigma-Aldrich, St. Louis, Mo.). Any of these and other related chemicals is effective as a replacement of TWEEN® 20.

An effective amount of non-ionic detergent for selective binding of double-stranded nucleic acid could vary slightly among the different detergents. However, the optimal concentration for each detergent can be easily identified by some simple experiments. In general, it is discovered that a final concentration of detergent at 0.5% or greater is effective for selective binding of the double-stranded nucleic acid. In certain embodiments, the effective concentration is between 0.5% and about 10%. In a preferred embodiment, the concentration is between 1% and about 5%. It is also noted that more than one non-ionic detergents can be combined, as long as the combined concentration of the detergents is within the range of 0.5% to about 10%.

When the sample is a biological sample or cells, it is first lysed in an aqueous lysis system containing chaotropic substances and/or other salts by, in the simplest case, adding it to the cells. Some biological sample or cells cannot be lysed directly in aqueous systems containing chaotropic substances, such as bacteria, for instance, due to the condition of their cell walls. These starting materials must be pretreated, for example, with lytic enzymes, prior to being used in the process according to the invention. Preferably, the lysis solution also includes a reducing agent which facilitates denaturization of RNase by the chaotropes and aids in the isolation of undegraded RNA.

The lysis solution of the present invention preferably also contains a sufficient amount of buffer to maintain the pH of the solution.

The mineral support preferably includes porous or non-porous metal oxides or mixed metal oxides, silica gel, silica membrane, materials predominantly consisting of glass, such as unmodified glass particles, powdered glass, quartz, alumina, zeolites, titanium dioxide, zirconium dioxide. The particle size of the mineral support material ranges from 0.1 μm to 1000 μm, and the pore size from 2 to 1000 μm. Said porous or non-porous support material may be present in the form of loose packings or may be embodied in the form of filter layers made of glass, quartz or ceramics, and/or a membrane in which silica gel is arranged, and/or particles or fibers made of mineral supports and fabrics of quartz or glass wool, as well as latex particles with or without functional groups, or frit materials made of polyethylene, polypropylene, polyvinylidene fluoride, especially ultra high molecular weight polyethylene, high density polyethylene.

The flow-through from the first mineral support contains single-stranded nucleic acid (e.g., total RNA). It is discovered that at reduced non-ionic detergent concentration, single-stranded nucleic acid (e.g., RNA) binds to the mineral support. The flow-through is thus adjusted to a lower non-ionic detergent concentration and applied to a second mineral support. A simple centrifugation step separates the single-stranded nucleic acid bound to the mineral support from the second flow-through.

Typically, the flow-through from the first mineral support is diluted to a non-ionic detergent level of less than about 1%, such as less than 0.5% or even less than 0.1%. This is generally achieved using a solution having a composition similar to the solution used for initial mixing of the sample prior to loading of the first mineral support, other than that this second solution has a reduced or null level of non-ionic detergent.

Alternatively the flow-through can be mixed with a lower aliphatic alcohol such as 70% ethanol, followed by loading to and purification from the second column. In addition, the flow-through can be recovered by a variety of other methods available. These include alcohol precipitation or other chromatography separation methods.

The second mineral support for single-stranded nucleic acid binding includes a similar material as the first mineral support described above. Preferably, the first mineral support and the second mineral support are each silica membranes.

The double-stranded nucleic acid adsorbed on the first mineral support and the single-stranded nucleic acid adsorbed on the second mineral support can be eluted under conditions of low ionic strength or with water, respectively.

Wash steps may be performed prior to the elution of the respective nucleic acid (single-stranded nucleic acid or double-stranded nucleic acid). For purifying the double-stranded genomic DNA, a wash of the first mineral support (i.e., column) can be applied to removes any residual single-stranded nucleic acid. This wash is performed with a solution similar in composition to the double-stranded nucleic acid binding solution containing chaotropic salt and a high non-ionic detergent level. Further, a wash buffer containing a high concentration of organic solvents such as lower aliphatic alcohols, can also be used to wash the first and second mineral support prior to elution of the desired nucleic acid, to remove components other than the bound nucleic acids.

Following the work flow illustrated in FIG. 1 and the experimental conditions as further described in the Examples below, double-stranded and single-stranded nucleic acids have been successfully purified from sample mixtures, with a high recovery rate.

Also provided is a kit for the separation and/or purification of double-stranded and single-stranded nucleic acids from a sample. The kit comprises: a solution containing a chaotropic salt and one or more non-ionic detergents for sample processing; a first mineral support for binding the double-stranded nucleic acid; a second mineral support for binding the single-stranded nucleic acid; an elution solution for eluting double-stranded nucleic acid from the first mineral support; and an elution solution for eluting single-stranded nucleic acid from the second mineral support.

Preferably, the sample processing solution in the kit includes a chaotropic salt, a non-ionic detergent and a pH buffer. Most preferably, the solution includes 7 M guanidine HCl, 50 mM Tris, pH 5 and 0.5-10% of a non-ionic detergent.

The mineral support may be present in loose packing, fixed between two means (for example frits, plugs made out of a suitable inert material, etc), or in the form of membranes which are arranged within the hollow body of a column. Preferably, the first mineral support and the second mineral support are each silica membranes.

Other features and advantages of the invention will be apparent from the following examples and from the claims.

EXAMPLES

The following examples serve to illustrate the process for the separation and purification of double-stranded and single-stranded nucleic acids from a sample according to embodiments of the present invention and are not intended to be limiting.

Solutions and Protocols
1. Solutions and Columns Used in the Examples

| Description | Composition |
| --- | --- |
| Double-stranded nucleic acid binding solution | 7M Guanidine HCl, 50 mM Tris, pH 5, 1% TCEP (optional), plus non-ionic detergent |
| Wash buffer | 10 mM Tris, 1 mM EDTA, pH 8 (before use, 4 parts of ethanol added to 1 part of buffer) |
| Double-stranded nucleic acid elution buffer | 10 mM Tris, 0.5 mM EDTA, pH 8 |
| Single-stranded nucleic acid elution buffer | Water |
| ILLUSTRA ™ genomicPrep tissue and cell mini column | silica membrane spin column |

2. Double-Stranded Nucleic Acid Purification
2.1 Double-Stranded Nucleic Acid Binding
a. Place a new spin column into a new collection tube.
b. Transfer ~350 μl mixture of the sample containing both double-stranded and single-stranded nucleic acid and the double-stranded nucleic acid binding solution (including an effective amount of non-ionic detergent) to the column.
c. Centrifuge at 11,000×g for 1 min.
d. Save the flow-through for purification of single-stranded nucleic acid.
e. Transfer the column to a new 2 ml collection tube.

2.2 Column Wash
a. Add 500 µl of the double-stranded nucleic acid binding solution to the column
b. Centrifuge at 11,000×g for 1 min. Discard the flow through.
c. Place the column back into the same collection tube.
d. Add 500 µl of Wash buffer to the column
e. Centrifuge at 11,000×g for 1 min.
f. Transfer the column to a clean 1.5 ml microcentrifuge tube.
2.3 Double-Stranded Nucleic Acid Elution
a. Add 100 µl Elution buffer to the center of the column
b. Centrifuge at 8,000×g for 1 minute.
c. Discard the column and store the tube containing pure double-stranded nucleic acid at −20° C.
3. Single-Stranded Nucleic Acid Purification
3.1 Single-Stranded Nucleic Acid Binding
a. Place a new spin column in a new collection tube.
b. Mixing the flow-through from step 2.1.d with a double-stranded nucleic acid binding solution (without non-ionic detergent) to reduce the level of non-ionic detergent in the mixture. Mix well by pipetting up and down several times. Transfer the entire mixture to the column (repeat steps c. and d. if needed to run all the mixture through a column).
c. Centrifuge at 11,000×g for 1 min.
d. Discard the flow-through.
e. Transfer the column to a new 2 ml collection tube.
3.2 Column Wash
a. Add 500 µl of Wash Buffer to the column
b. Centrifuge at 11,000×g for 1 min.
c. Transfer the column to a clean 1.5 ml microcentrifuge tube.
3.3 Single-Stranded Nucleic Acid Elution
a. Add 100 µl of Elution buffer to the center of the column.
b. Centrifuge at 8,000×g for 1 minute.
c. Discard the column and store the tube containing single-stranded nucleic acid at −20° C. (DNA) or −80° C. (RNA) until needed.

Example 1

Separation and Purification of a Sample Containing Both Genomic DNA and Total RNA To find an optimal protocol for the separation (and purification) of double-stranded and single-stranded nucleic acids, we experimented with a mixture of purified genomic DNA and purified RNA. Effective separation was achieved using the following method.

We mixed 2 µg of purified rat liver genomic DNA and 2 µg of purified rat liver total RNA with the above double-stranded nucleic acid binding solution, with varying amount of non-ionic detergent. We then followed the protocol above for double-stranded nucleic acid purification. We found that a solution with a working composition of 7 M Guanidine HCl, 50 mM Tris, pH 5, plus a relatively high concentration of non-ionic detergent is optimal for selective binding of DNA to the first column. We also found that a reduction in the concentration of the non-ionic detergent enables RNA binding to the column. A simple dilution of the flow through thus will allow RNA to bind to the second column.

Figure 2:
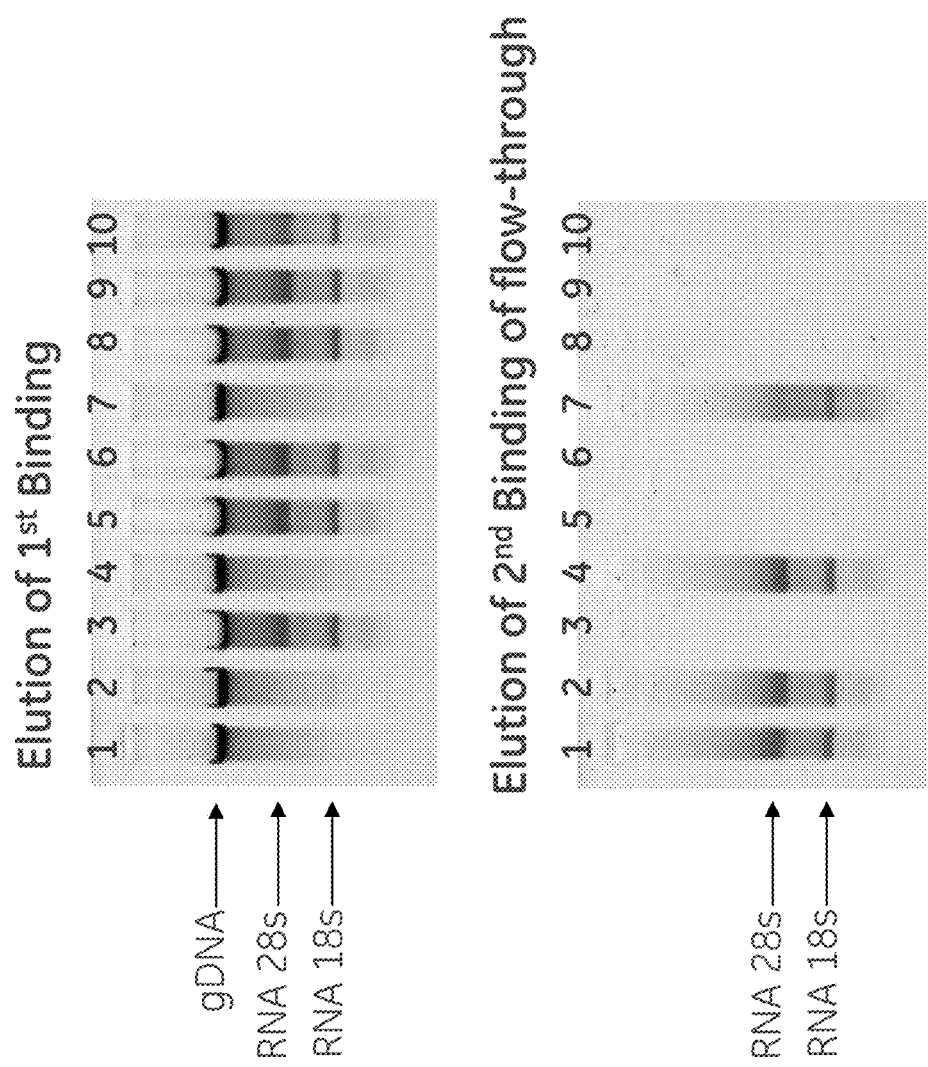
FIG. 2 shows gel images of genomic DNA and total RNA separation according to an example in the experimental section. Top panel shows nucleic acid eluted from the first column. Bottom panel shows total RNA eluted from the second column.

FIG. 2 presents data for representative experiments of genomic DNA and total RNA separation, showing successful separation using the current process. The starting material each contained 2 µg of purified genomic DNA and 2 µg of purified total RNA (2 µl each). They are mixed with the double-stranded nucleic acid binding solution (350 µl of 7 M Guanidine HCl, 50 mM Tris, pH 5 with varying amount of non-ionic detergent). The above protocols were followed unless noted below. The flow through from the first column was mixed with 250 µl EtOH and applied to a second silica membrane column to examine the content of the first flow through. (It is known that under this condition both double and single-stranded nucleic acid will bind to the column.) Elution from both columns was performed in 100 µl volume, and 15 µl was loaded for an agarose gel electrophoresis analysis.

TWEEN® 20 was used as the non-ionic detergent in the first set of experiments, at 5% (lanes 1), 1% (lanes 2) and 0.1% (lanes 3). It is apparent that at 5% TWEEN® 20, only genomic DNA became bound to the silica membrane column, RNA did not (lane 1, top panel). It is also apparent that all genomic DNA became bound to the first column, and no genomic DNA was present in the first flow through (bottom panel, lane 1). At 1% TWEEN® 20, slight RNA binding to the first column was observed (lane 2, top panel). At 0.1% TWEEN® 20, all the RNA became bound to the first column, no nucleic acid was present in the first flow through (lanes 3 of top and bottom panel).

In the second set of experiments, NP-40 was used as the non-ionic detergent, again at 5% (lanes 4), 1% (lanes 5) and 0.1% (lanes 6). It is apparent that at 5% NP-40, only genomic DNA became bound to the silica membrane column, RNA did not (lane 4, top panel). It is also apparent that all genomic DNA became bound to the first column, and no genomic DNA was present in the first flow through (bottom panel, lane 4). At 1% or 0.1% NP-40, all the RNA became bound to the first column, and no nucleic acid was present in the first flow through (lanes 5 and 6 of top and bottom panels).

In the set of third experiment, TRITON® X-100 was used as the non-ionic detergent, again at 5% (lanes 7), 1% (lanes 8) and 0.1% (lanes 9). It is apparent that, similar to NP-40, at 5% TRITON® X-100, only genomic DNA became bound to the silica membrane column, RNA did not (lane 7, top panel). It is also apparent that all genomic DNA became bound to the first column, and no genomic DNA was present in the first flow through (bottom panel, lane 7). At 1% or 0.1% TRITON® X-100, all the RNA became bound to the first column, and no nucleic acid was present in the first flow through (lanes 8 and 9 of top and bottom panels).

As a control, in the absence of a non-ionic detergent, both genomic DNA and total RNA became bound to the first silica membrane column (lanes 10 of top and bottom gel panels).

The experiments demonstrate that at pH 5, genomic DNA in a solution containing chaotropic salt and a high concentration of a non-ionic detergent would bind to the silica membrane column, but RNA will not bind. However, at reduced level of the detergent, both will bind to the column. A simple adjustment of the concentration of the non-ionic detergent of the flow-through enables RNA binding to the column. This adjustment achieves similar effect for RNA binding as the use of a lower aliphatic alcohol.

All patents, patent publications, and other published references mentioned herein are hereby incorporated by reference in their entireties as if each had been individually and specifically incorporated by reference herein. While preferred illustrative embodiments of the present invention are described, one skilled in the art will appreciate that the present invention can be practiced by other than the described embodiments, which are presented for purposes of illustration only and not by way of limitation. The present invention is limited only by the claims that follow.

What is claimed is:

1. A method for the separation of double-stranded nucleic acid from single-stranded nucleic acids, which method comprising:

a) mixing a sample containing said double-stranded nucleic acid and said single-stranded nucleic acid with a solution containing (1) a chaotropic salt and (2) one or more non-ionic detergent having a combined concentration of from 0.5% to 10% to generate a mixture;
b) applying said mixture to a first mineral support for the double-stranded nucleic acid to bind;
c) collecting a flow-through which contains unbound single-stranded nucleic acid;
d) diluting the one or more non-ionic detergent of said flow-through to 0.1%; and
e) applying the adjusted flow-through from step (d) to a second mineral support for the single-stranded nucleic acid to bind.

2. The method of claim 1, further comprising recovering the double-stranded nucleic acid from the first mineral support.

3. The method of claim 2, further comprising washing the first mineral support prior to the recovery of the double-stranded nucleic acid.

4. The method of claim 1, further comprising recovering the single-stranded nucleic acid from the second mineral support.

5. The method of claim 4, further comprising washing the second mineral support prior to the recovery of the single-stranded nucleic acid.

6. The method of claim 1, wherein said double-stranded nucleic acid is double-stranded DNA and said single-stranded nucleic acid is RNA.

7. The method of claim 1, wherein said sample is a lysate of cultured cells, microorganisms, plant or animal cells.

8. The method of claim 1, wherein the concentration of said one or more non-ionic detergent in said solution is between 1-5%.

9. The method of claim 1, wherein the concentration of said one or more non-ionic detergent in said solution is about 5%.

10. The method of claim 1, wherein said one or more non-ionic detergent is selected from the group consisting of NP-40, Triton X-100, Tween 20, and a combination thereof.

11. The method of claim 1, wherein said chaotropic salt is guanidine HCl.

12. The method of claim 1, wherein said pH-neutral, buffered solution has a pH of about 5.0, includes about 7 M guanidine HCl, 50 mM Tris-HCl, and a non-ionic detergent of about 5%.

13. The method of claim 1, wherein the first mineral support and the second mineral support are porous or non-porous and is metal oxides, mixed metal oxides, silica gel, silica membrane, glass particles, powdered glass, quartz, alumina, zeolite, titanium dioxide, or zirconium dioxide.

14. The method of claim 11, wherein the first mineral support and the second mineral support are each silica membranes.

15. The method of claim 1, wherein step d) comprises diluting the flow-through with a lower aliphatic alcohol.

16. The method of claim 15, further comprising recovering the single-stranded nucleic acid from the second mineral support; and optionally washing the second mineral support prior to the recovery of the single-stranded nucleic acid.

17. The method of claim 15, wherein the lower aliphatic alcohol is ethanol.

* * * * *